United States Patent
Powell et al.

(10) Patent No.: US 11,452,555 B2
(45) Date of Patent: Sep. 27, 2022

(54) BONE FRACTURE FIXATION CLAMP

(71) Applicant: DePuy Synthes Products, Inc., Raynham, MA (US)

(72) Inventors: Sean Powell, West Chester, PA (US); Robert Limouze, West Chester, PA (US); Natasha Weeks, West Chester, PA (US); Rene Haag, West Chester, PA (US); George J. Haidukewych, Orlando, FL (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 611 days.

(21) Appl. No.: 16/520,994

(22) Filed: Jul. 24, 2019

(65) Prior Publication Data
US 2019/0343563 A1 Nov. 14, 2019

Related U.S. Application Data

(63) Continuation of application No. 15/981,560, filed on May 16, 2018, now Pat. No. 10,376,297, which is a continuation of application No. 13/468,622, filed on May 10, 2012, now Pat. No. 9,999,456, which is a
(Continued)

(51) Int. Cl.
| A61B 17/82 | (2006.01) |
| A61B 17/84 | (2006.01) |
| A61B 17/68 | (2006.01) |
| A61F 2/36 | (2006.01) |

(Continued)

(52) U.S. Cl.
CPC .............. *A61B 17/84* (2013.01); *A61B 17/68* (2013.01); *A61B 17/82* (2013.01); *A61B 17/80* (2013.01); *A61B 17/86* (2013.01); *A61B 2017/681* (2013.01); *A61F 2/36* (2013.01)

(58) Field of Classification Search
CPC ... A61B 2017/681; A61B 17/82; A61B 17/08; A61B 17/2808
See application file for complete search history.

(56) References Cited

U.S. PATENT DOCUMENTS

| 408,080 A | 7/1889 | Carroll |
| 556,239 A | 3/1896 | Ashald et al. |
| 995,411 A | 6/1911 | Morrill |

(Continued)

FOREIGN PATENT DOCUMENTS

| CN | 2442646 | 8/2001 |
| CN | 201701282 | 1/2011 |
| JP | 11347046 | 12/1999 |

*Primary Examiner* — David W Bates
(74) *Attorney, Agent, or Firm* — Fay Kaplun & Marcin, LLP

(57) ABSTRACT

A bone fixation clamp includes a first arcuate clamp member conforming to a shape of a bone and extending between a first connection end and a first free end, a second arcuate clamp member conforming to a shape of the bone, a second connection end of the second clamp member being pivotally attached to the first clamp member, the second clamp member extending between the second connection end and a second free end and a driving member received in the first clamp member passing out of the first clamp member to abut an abutment portion of the second member so that, as the driving member is extended further out of the first member, the driving member pivots the second clamp member relative to the first clamp member to draw the first and second free ends toward one another to apply a radially compressive force to the bone.

20 Claims, 11 Drawing Sheets

Related U.S. Application Data continuation-in-part of application No. 13/068,397, filed on May 10, 2011, now abandoned.

(51) Int. Cl.
   *A61B 17/80* (2006.01)
   *A61B 17/86* (2006.01)

(56) References Cited

U.S. PATENT DOCUMENTS

| | | |
|---|---|---|
| 1,156,440 A | 10/1915 | Smith |
| 1,239,595 A | 9/1917 | Rawthorne |
| 1,304,503 A | 5/1919 | Miller |
| 1,977,725 A | 10/1934 | Heidbrink |
| 2,362,957 A | 11/1944 | Hackett |
| 2,460,470 A | 2/1949 | Rogers |
| 2,966,907 A | 1/1961 | Fasolino |
| 3,385,299 A | 5/1968 | Roy |
| 3,477,429 A | 11/1969 | Sampson |
| 4,201,215 A | 5/1980 | Crossett et al. |
| 4,263,904 A | 4/1981 | Judet |
| 5,797,919 A | 8/1998 | Brinson |
| 6,051,007 A | 4/2000 | Hogendijk et al. |
| 8,231,623 B1 | 7/2012 | Jordan |
| 8,267,957 B1 | 9/2012 | Silver |
| 8,500,073 B2 | 8/2013 | Quesnel |
| 8,579,950 B1 | 11/2013 | Jordan |
| 8,685,037 B1 | 4/2014 | Jordan |
| 2003/0225416 A1 | 12/2003 | Bonvallet et al. |
| 2004/0059335 A1 | 3/2004 | Weaver et al. |
| 2005/0126563 A1 | 6/2005 | Van Der Burg et al. |
| 2009/0062869 A1 | 3/2009 | Claverie |
| 2010/0222793 A1 | 9/2010 | Skipper |
| 2014/0155903 A1 | 6/2014 | Soliman |

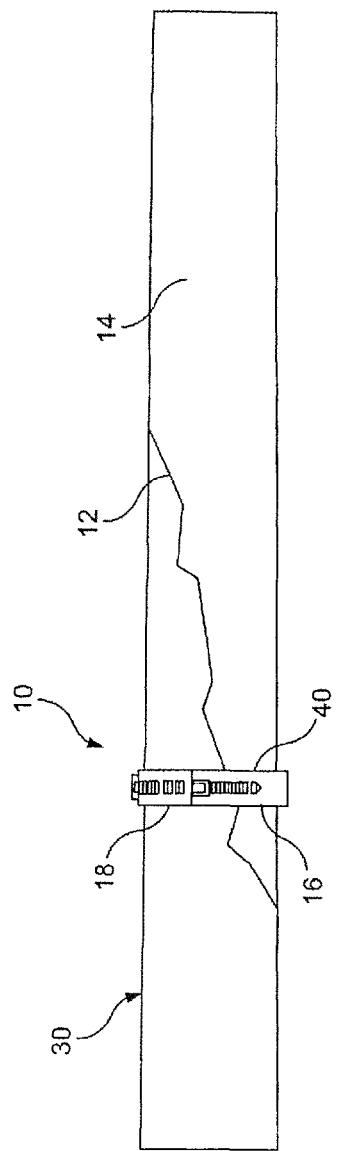

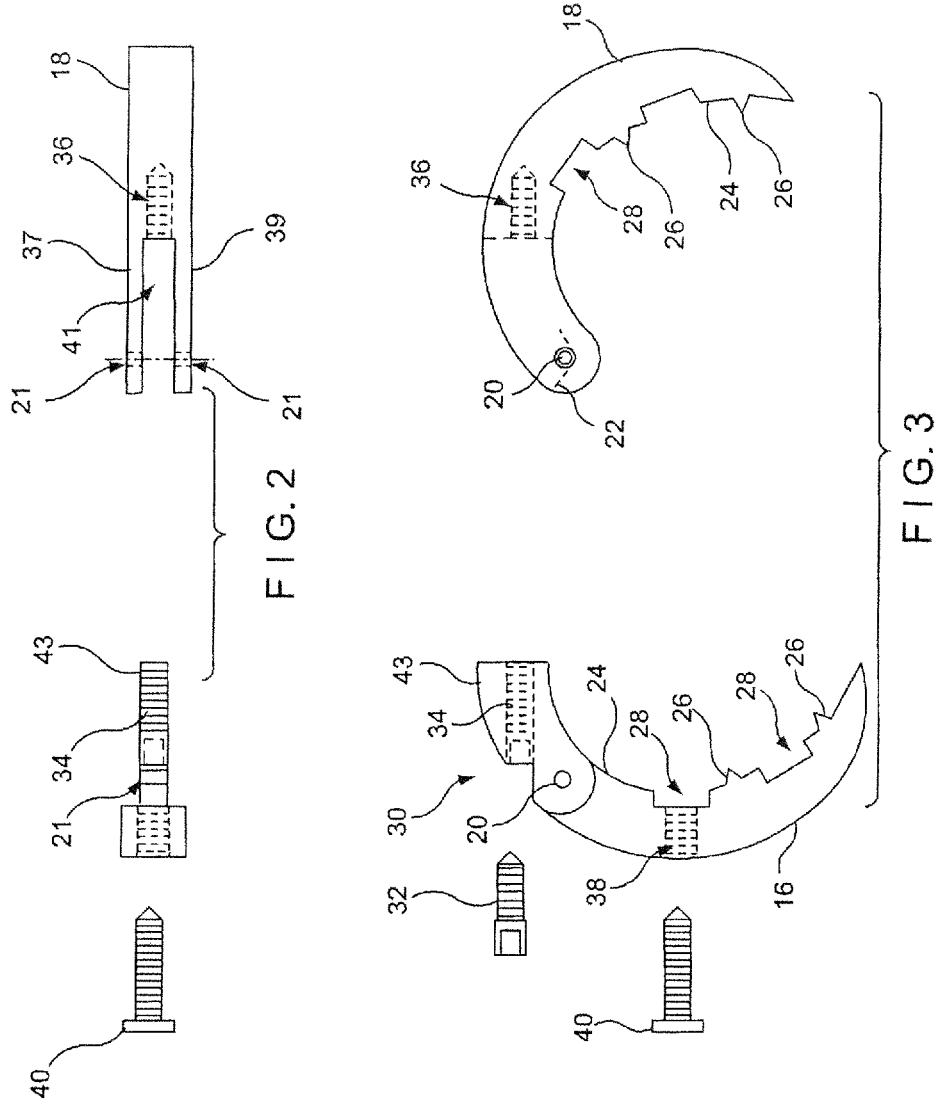

BONE FRACTURE FIXATION CLAMP

PRIORITY CLAIM

The present application is a Continuation Application of U.S. patent application Ser. No. 15/981,560 filed on May 16, 2018; which is a Continuation Application of U.S. patent application Ser. No. 13/468,622 filed on May 10, 2012, now U.S. Pat. No. 9,999,456; which is a Continuation-in-Part Application of U.S. patent application Ser. No. 13/068,397 filed on May 10, 2011. The disclosure of the above patent(s)/application(s) is incorporated herein by reference.

FIELD OF THE INVENTION

The present invention relates to the fixation of fractured bones and, in particular, relates to a system and method for securing a bone fixation clamp over an outer periphery of a fractured bone.

BACKGROUND

Fractures of long bones are sometimes treated by bone fixation devices that are positioned over an outer periphery of the bone. For example, the fixation of long oblique fractures in bones previously fitted with metal prostheses (e.g. intramedullary nails) precludes the use of bone fixation devices that extend into the bone. Such bone fixation procedures therefore use a combination of cables, clamps and metal compression plates which are employed with or without fixation screws that extend into the bone. A number of prior art examples are discussed below.

SUMMARY OF THE INVENTION

The present invention is directed to a bone fixation clamp comprising a first arcuate clamp member conforming to a shape of a target portion of a bone and extending between a first connection end and a first free end and a second arcuate clamp member conforming to a shape of the target portion of the bone, a second connection end of the second clamp member being pivotally attached to the first connection end of the first clamp member, the second clamp member extending between the second connection end and a second free end. The bone fixation clamp further comprises a driving member received in the first clamp member passing out of the first clamp member to abut an abutment portion of the second member so that, as the driving member is extended further out of the first member, the driving member pivots the second clamp member relative to the first clamp member to draw the first and second free ends toward one another to apply a radially compressive force to the bone.

BRIEF DESCRIPTION OF THE DRAWINGS

FIG. 1 is a side view of the fixation clamp according to a first embodiment of the present invention secured in operative position on a fractured bone;

FIG. 2 is an exploded top view of the fixation clamp of the present invention;

FIG. 3 is a partial side view of the fixation clamp of the present invention;

DETAILED DESCRIPTION

Figure 4:
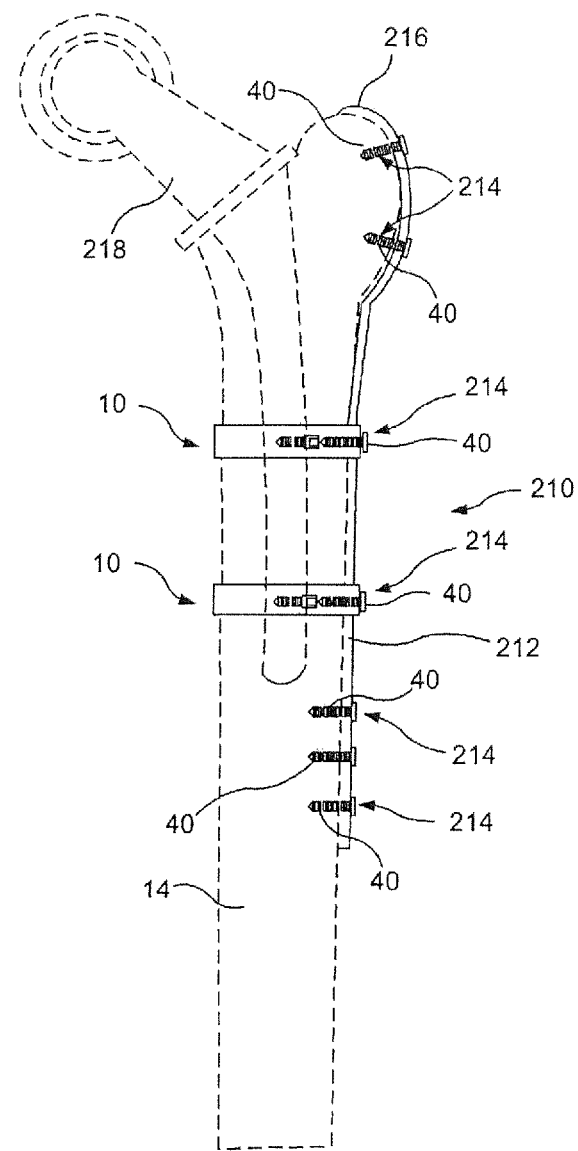
FIG. 4 is a side view of a fractured bone with a plurality of fixation clamps of the present invention in combination with an elongated plate secured in operative position on the fractured bone.

The present invention may be further understood with reference to the following description and the appended drawings, wherein like elements are referred to with the same reference numerals. The present invention relates to the treatment of fractured bones and, in particular, relates to a system and method for stabilizing a fractured or otherwise damaged bone by securing a bone fixation device to an outer surface thereof. The exemplary system and method according to the invention may be used for the fixation of fractures in a long bone (e.g., oblique fractures, transverse fractures, etc.) or to add strength and stability to a weakened bone (e.g., due to osteoporosis). An exemplary bone stabilization device according to the invention includes first and second clamp members having an arcuate shape conforming to an outer surface of a bone to which the first and second clamp members are to be attached. In one embodiment of the invention, the first and second clamp members may be removably attachable to one another such that the first and second clamp members are individually insertable into the body and over the bone in a target orientation. In another embodiment, the first and second clamp members are permanently attached to one another and permitted to move relative to one another within a predetermined range of motion. The first and second clamp members include respective attachment portions configured to interlock one another. The first and second attachment portions include a provisional attachment mechanism configured to provisionally hold the first and second clamp members together and permit a limited movement of the first and second clamp members relative to one another such that little or no compression is applied to the bone. As will be described in greater detail later on, the provisional attachment mechanism may be one of a pivot joint, a sliding joint, a ratcheted joint or a threaded joint. The first and second attachment portions further comprise a locking mechanism configured to draw the first and second clamp members radially inward to apply a compressive force to the bone. The locking mechanism may be a screw configured for threaded insertion through respective holes in the first and second clamp members. In an operative configuration, once the first and second clamp members have been provisionally secured to the bone, the screw may be inserted through the respective holes to draw the first and second clamp members to a tightened configuration over the bone, radially compressing the bone. In another embodiment of the invention, a bone plate may be inserted over the bone prior to or after insertion of the first and second clamp members so that the first and second clamp members also secure the bone plate to the hone, as will be described in greater detail later on. It will be understood by those of skill in the art that although the exemplary embodiments specifically describe a device for a stabilization of a fractured long bone, the device of the present invention may be used for any bone through which it is desirable to secure the exemplary stabilization device.

As shown in FIGS. 1 and 2, the present invention relates to a fixation clamp generally indicated as 10 to stabilize a spiral bone fracture 12 in an elongated tubular bone 14. The fixation clamp 10 comprises a first arcuate clamp member 16 and a second arcuate clamp member 18 (a pair of clamp members) pivotally coupled or hinged to each other by a hinge or pivot pin 20 operatively disposed in channels or holes 21 formed in each of the clamp members 16 and 18. A bias or spring 22 is disposed adjacent the hinge or pivot pin 20 to normally bias the first arcuate clamp member 16 and the second clamp member 18 in an open position relative to each other.

Each arcuate clamp member 16 and 18 includes a concave inner surface 24 having at least one spike-like element or protrusion 26 extending outwardly from each concave inner surface 24 to engage the surface of the bone 14 to secure the fixation clamp 10 in place. In addition, a plurality of pressure relief recesses or indentations each indicated as 28 is formed in the concave inner surface 24 of each clamp member 16 and 18 to preserve the blood flow in the patient's limb when the fixation clamp 10 is secured in position.

As shown in FIGS. 2 and 3, the fixation clamp 10 further includes an adjustment device generally indicated as 30 to tighten the arcuate clamp members 16 and 18 around the bone 14 forcing the spike-like elements or protrusions 26 into the surface of the bone 14. The adjustment device 30 comprises an externally threaded member 32 configured to be threaded through an internally threaded channel or portion 34 formed in the first arcuate clamp member 16 adjacent the hinge or pivot pin 20 and into an internally threaded portion or recess 36 formed in the second arcuate clamp member 18 adjacent the hinge or pivot pin 20 to tighten and secure the fixation clamp 10 in place around the hone 14.

The second arcuate clamp member 18 includes an upper plate or flange 37 and a lower plate or flange 39 disposed in spaced relationship relative to each other to cooperatively form a slot or opening 41 therebetween to receive an extension or tongue 43 including the internally threaded channel or portion 34 formed on the first arcuate clamp member 16. The fixation clamp 10 may further include at least one internally threaded aperture or channel 38 formed through one or both arcuate clamp members 16 and 18 to receive an externally threaded anchoring screw or fastener 40 screwed into the bone 14 to anchor the fixation clamp 10 in place.

Figure 5:
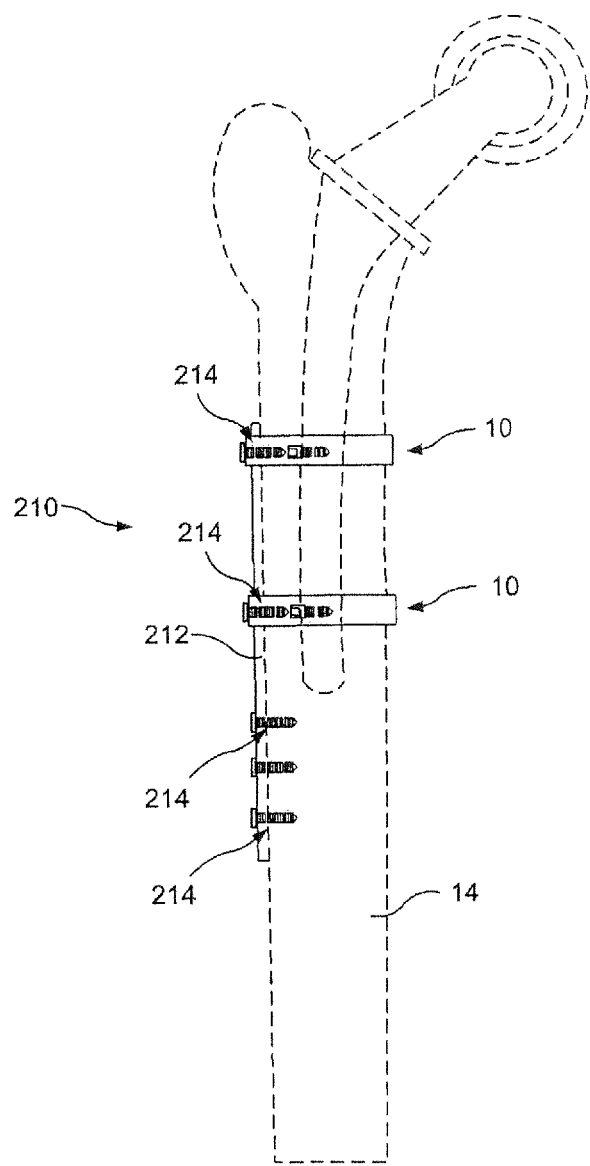
FIG. 5 is a side view of a fractured bone with a plurality of fixation clamps embodying the present invention in combination with an elongated plate secured in operative position on a fractured bone.

FIGS. 4 and 5 show the fixation clamp 10 in use as part of a fixation assembly. Specifically, in addition to the fixation clamp 10, the fixation assembly includes a bone plate generally indicated as 210 comprising an elongated plate member 212 having a plurality of internally threaded apertures each indicated as 214 formed along the length thereof and a trochanteric grip portion 216 formed on the upper end portion of the elongated plate member 212 having at least one internally threaded aperture 218 to receive a corresponding plurality of externally threaded screws or fasteners 40 to secure the bone plate 210 to the patient's bone 14 including the femur adjacent the hip prosthesis 218. At least one fixation clamp 10 is then placed around the bone 14 and over the elongated plate member 212 of the bone plate 210 aligning the internally threaded aperture 38 of one of the pair of clamp members 16 and 18 with corresponding internally threaded aperture 214 to insert a corresponding anchoring screw or fastener 40 therethrough and into the bone 14.

Figure 6:
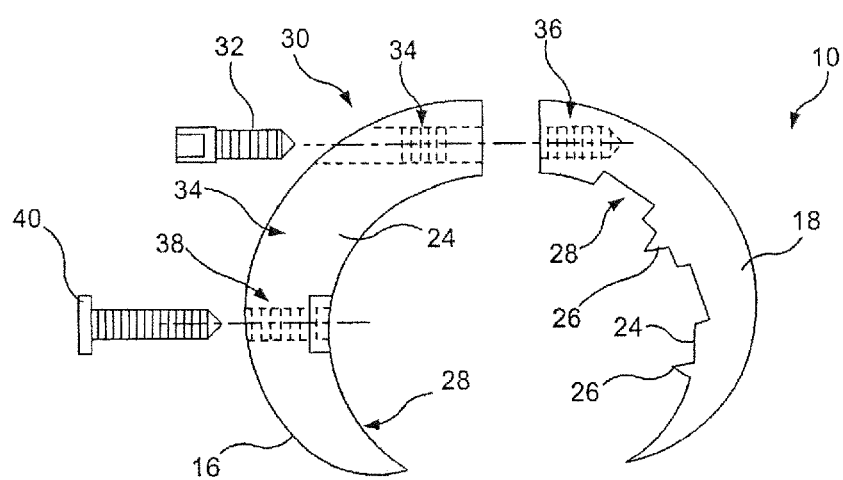
FIG. 6 is a top view of a fixation clamp according to a first alternate embodiment of the invention.

FIG. 6 shows an alternate embodiment of the present invention. Specifically, the fixation clamp 10 comprises a first arcuate clamp member 16 and a second arcuate clamp member 18 (a pair of separate clamp members).

Each arcuate clamp member 16 and 18 includes a concave inner surface 24 at least one of which has at least one spike-like element or protrusion 26 extending outwardly from the concave inner surface 24 to engage the surface of the bone 14 to secure the fixation clamp 10 in place. In addition, at least one pressure relief recess or indentation 28 is formed in the concave inner surface 24 of at least one of the clamp members to preserve the blood flow in the patient's limb when the fixation clamp 10 is secured in position.

The fixation clamp 10 further includes an adjustment device generally indicated as 30 to tighten the arcuate clamp members 16 and 18 together around the bone 14 forcing the spike-like element or protrusion 26 into the surface of the bone 14. The adjustment device 30 comprises an externally threaded member 32 configured to be threaded through an internally threaded portion or channel 34 formed in the first arcuate clamp member 16 and into an internally threaded portion or recess 36 formed in the second arcuate clamp member 18 to tighten and secure the fixation clamp 10 in place around the bone 14.

Figure 7:
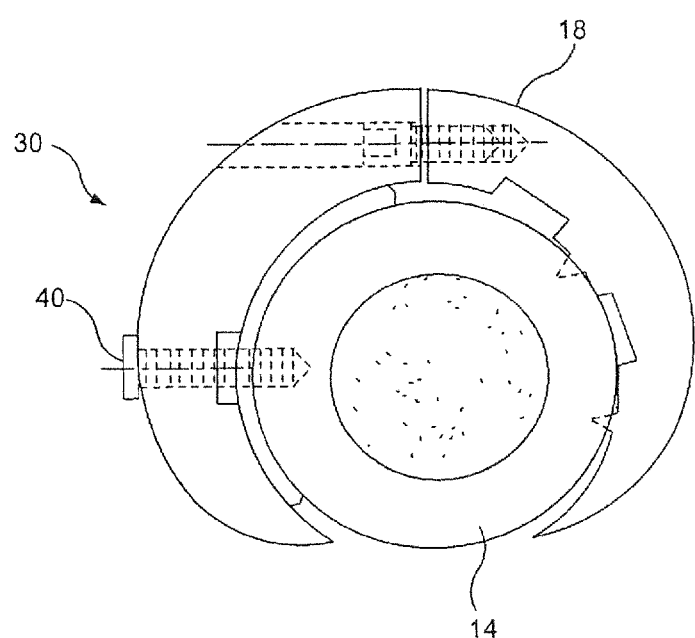
FIG. 7 is a top view of the fixation clamp shown in FIG. 6 operatively affixed to the bone of a patient.

As best shown in FIG. 7, the first arcuate clamp member 16 and the second arcuate clamp member 18 do not fully encircle the bone 14 leaving a space between the free or distal ends to insure continued circulation.

Figure 8:
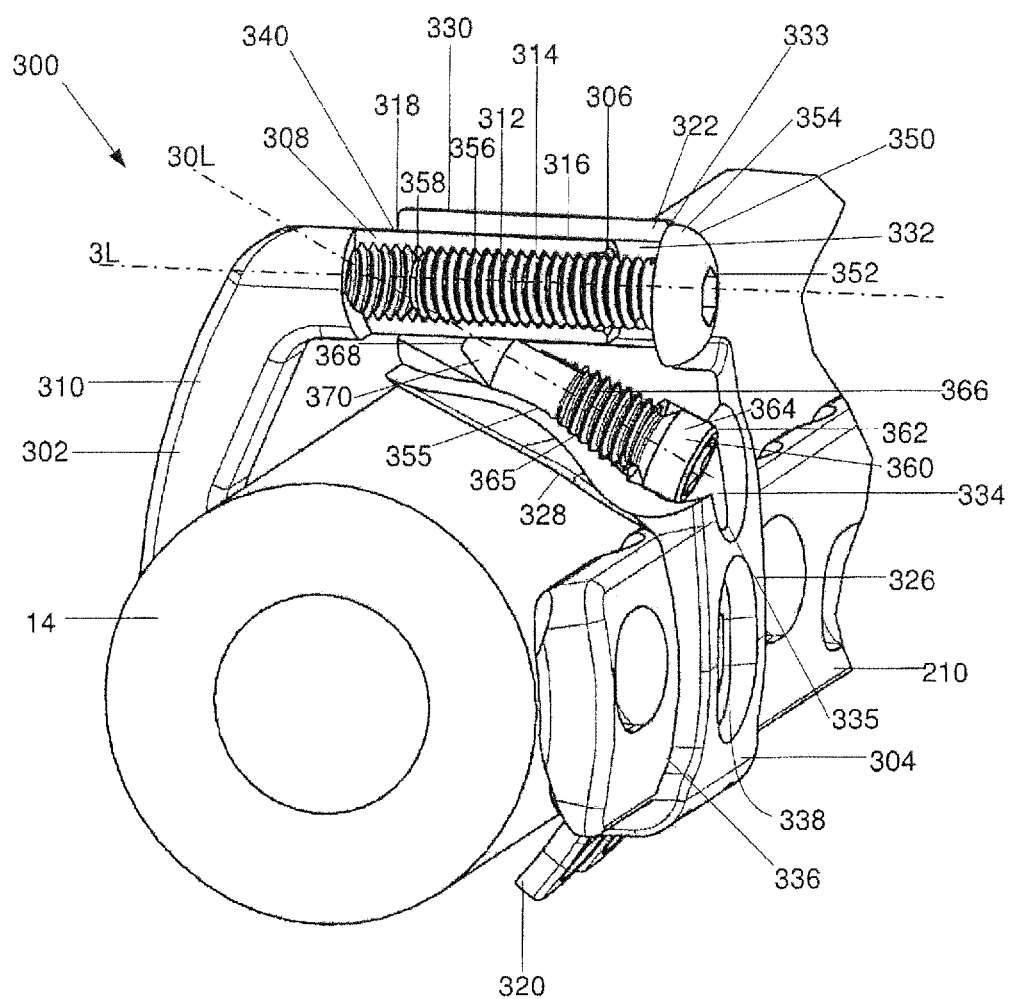
FIG. 8 depicts an isometric cutaway view of a bone fixation clamp according to a second alternate embodiment of the invention.

FIG. 8 depicts a clamp assembly 300 according to another embodiment of the invention. The clamp assembly 300 includes first and second arcuate clamp members 302, 304 positionable over a bone 14. The first clamp member 302 extends from a first end 306 along a first arm 308 to an arcuate body 310 which terminates in a second end (not shown). The first arm 308 extends linearly away from the arcuate body 308 along an axis which, when the assembly 300 is positioned as desired over a target portion of bone, extends substantially parallel to a diameter of the bone 14 across which a clamping force is applied by the first and second clamp members 302, 304. The first arm 308 includes an elongated first channel 312 extending thereinto from the first end 306 along a longitudinal axis 3L. A length of the channel 312 is selected to conform to a length of a locking screw 350 to be inserted therein in an operative configuration, as will be described in greater detail later on. The first channel 312 according to this embodiment includes threading 314 threadedly engaging threading on a shaft 356 of the locking screw 350.

The second clamp member 304 extends from a first end 318 along a second arm 322 distally to an arcuate body 326 terminating in a second end 320 which, in this embodiment, is configured to engage a bone plate and hold it in contact with a target portion of the bone 14. The second arm 322 includes a first surface 328 contoured to correspond to a portion of bone it is to contact. In this embodiment, as the bone 14 is generally cylindrical, the surface 328 is similarly curved. An outer surface 330 of the second arm 322 opposite the surface 328 extends substantially parallel to the longitudinal axis 3L. The second arm 322 includes second and third channels 332, 334 extending therethrough from respective first ends 333, 335 to a common second end 340. The second channel 332 extends along the longitudinal axis 3L and is dimensioned to slidably receive a portion of the first arm 308 therein. The third channel 334 extends along an axis 30L angled with respect to and intersecting the longitudinal axis 3L such that a set screw 360 inserted therethrough extends into the second channel 332. As will be described in greater detail with respect to the exemplary method below, a conical tip 370 of the set screw 360 passes through the third channel 334 to frictionally engage the outer surface 316 of the first arm 308 to provisionally hold the first and second arms 308, 322 together prior to insertion of the locking screw 350 into the second channel 332.

The arcuate body 326 of the second arm 322 further comprises a relief recess or indentation 336 substantially similar to the relief recess 28 and configured to permit insertion of a bone plate 210 therethrough to be held against the bone 14, as described in greater detail with respect to earlier embodiments. As would be understood by those skilled in the art, the shape and size of the relief recess 336 may be modified to conform to the dimensions of the bone plate 210. The bone plate 210 may be any bone plate known in the art and may be selected to conform to the requirements of a target bone stabilization procedure. A portion of the arcuate body 326 at the relief recess 336 may include an opening 338 extending therethrough and configured to align with an opening in the bone plate 210 to optionally permit insertion of a bone fixation element (e.g., a bone screw) therethrough and into the bone, as those skilled in the art will understand.

In accordance with an exemplary method according to the invention, the first and second clamp members 302, 304 are positioned over a target portion of the bone 14 employing a known minimally invasive insertion device. Specifically, the first clamp member 302 may be removably attached to a manipulation instrument (not shown) which allows introduction and aids in positioning of the first clamp member 302 over the bone 14. The manipulation instrument (not shown) also guides insertion of the second clamp member 304 into the body and over the bone 14 to assemble the first and second clamp members 302, 304 to one another in-situ. As will be described in greater detail later on, the set screw 360 is positioned in the third channel 334 prior to insertion of the second clamp member 304 over the bone. Specifically, the set screw 360 may be initially housed in the third channel 334 in an insertion configuration in which the distal conical tip 370 does not intersect the second channel 332. In an exemplary embodiment the bone plate 210 is placed and locked to the bone 14 prior to the insertion of the clamp assembly 300. In another embodiment, the hone plate 210 is positioned between the relief recess 336 and the bone 10 after the clamp assembly has been provisionally secured to the bone. The first arm 308 is then slidably inserted into the end 340 and into the second channel 332 until engagement of the arcuate bodies 310, 326 with an outer surface of the bone 14 prevents further movement. Frictional engagement between the outer surface 316 of the first arm 308 and the second channel 332 prevents the first and second arms 302, 304 from inadvertently disengaging one another. The set screw 360 is then tightened into the first end 335 of the third channel 334 until the conical tip 370 frictionally engages the outer surface 316 of the first arm 308 to provisionally secure the first and second clamp members 302, 304 to the bone 14. The set screw 360 extends from a first end 362 having a head 364 and along a shaft 366 to a distal end 368 having the conical tip 370. A portion of the shaft 366 includes threading 365 engaging threading on an outer surface of the third channel 334. Engagement of the head 364 with a reduced diameter portion 335 of the third channel 334 prevents the set screw 360 from applying excessive force to the first arm 308. Once the first and second clamp members 302, 304 have been provisionally locked over the bone 14, the manipulation instrument is removed from the body.

The locking screw 350 is then inserted into the first end 333 of the second channel 332. The locking screw 350 extends from a first end 352 having a head 354 and along a threaded shaft 356 to a distal end 358. Threading of the shaft 356 is configured to engage the threads 314 of the first channel 312. The head 354 is dimensioned to prevent insertion thereof into the second channel 332. In an operative configuration, as the locking screw 350 is driven through the second channel 332 and into the first channel 312, the first and second clamp members 302, 302 are drawn toward one another to apply a radially compressive force to the bone 14.

Figure 9:
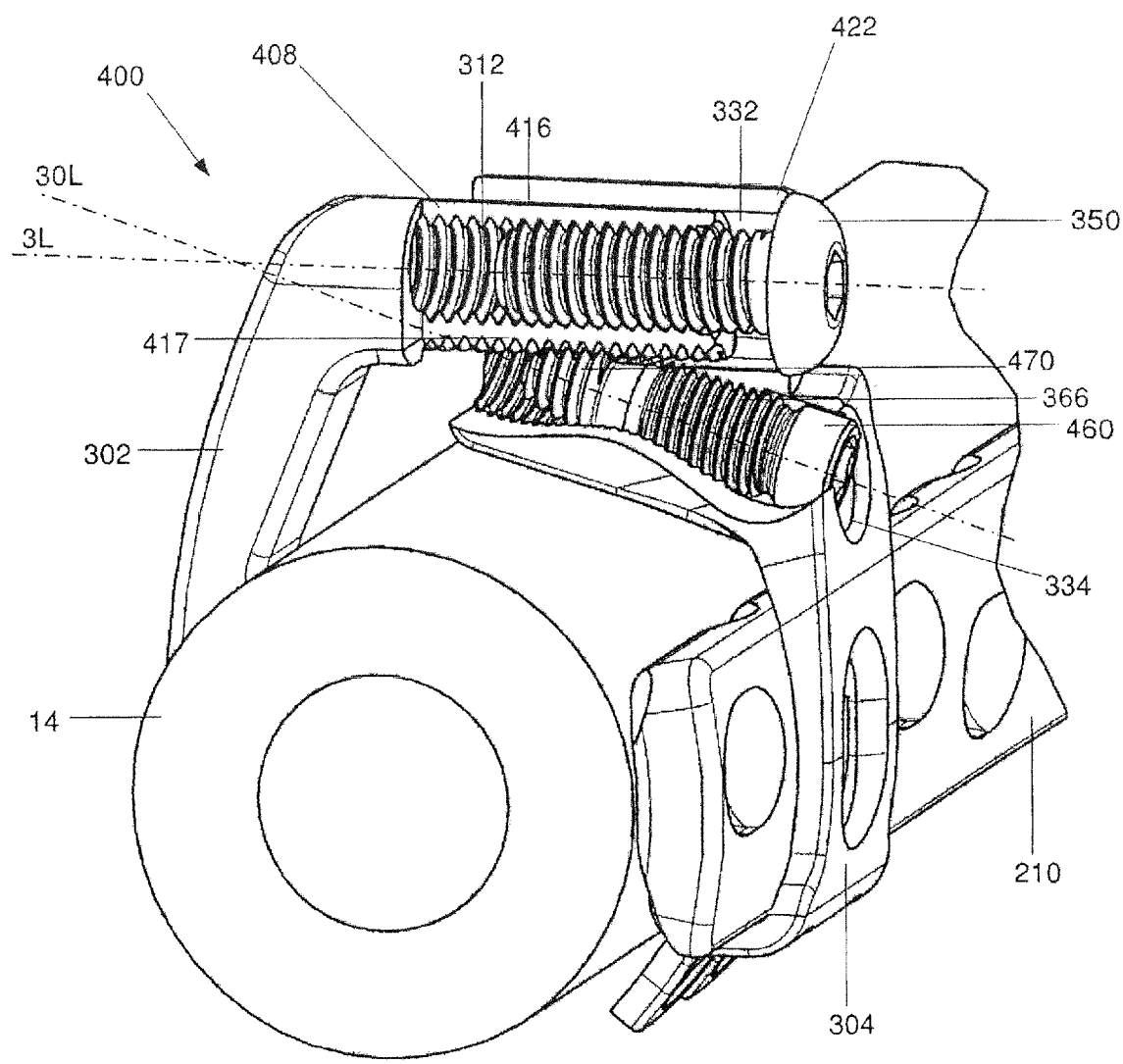
FIG. 9 depicts an isometric cutaway view of a bone fixation clamp according to a third alternate embodiment of the invention.

FIG. 9 depicts a clamp assembly 400 according to another embodiment of the invention. The clamp assembly 400 is formed substantially similarly to the clamp assembly 300 of FIG. 8, wherein like elements have been referenced with like reference numerals. The clamp assembly 400 includes the first and second clamp members 302, 304 including first and second arms 408, 422 substantially similar to the first and second clamp arms 308, 322. The clamp assembly 400 includes a locking screw 350 and a set screw 460 substantially similar to the locking screw 350 and the set screw 360. The set screw 460 extends from the first end 362 having the head 364 and along a threaded shaft 366 to a distal end 368 having a threaded tip 470. The threaded tip 470 includes threading 417 at a pitch corresponding to threading on an outer surface 416 of the first arm 408. The pitch of the threaded tip 470 may be greater than a pitch of the threaded shaft 366. It is noted, however, that the threaded tip 470 and the threaded shaft 366 may each be formed with any thread pitch without deviating from the scope of the invention.

In an exemplary embodiment, a portion of an outer surface 416 of the first arm 408 includes threading 417 threadedly engaging the threaded tip 470 of the set screw 460. The threading 417 extends along a length of the first arm 408 and may be formed on only a portion of the outer surface 416 which, in an operative configuration, is open to the third channel 334. An outlying portion of the outer surface 416 separate from the threading 417 may be substantially smooth. In another embodiment of the invention, the outer surface 416 may include one of teeth, a geared surface, or the like to engage a corresponding structure provided on either a surface of the second channel 432 or a distal end of a set screw to form a ratchet mechanism, as those skilled in the art will understand.

In accordance with an exemplary method of use of the clamp assembly 400, the first arm 408 is slidably inserted into the second channel 332 until the arcuate bodies 310, 326 contact an outer surface of the bone 14. The set screw 460 is then screwed into the first end 335 of the third channel 334 until the threaded tip 470 threadedly engages the threading 417 on the outer surface 416 of the first arm 408. Specifically, as described in greater detail earlier with respect to the clamp assembly 300, the set screw 460 may be partially inserted into the third channel 334 prior to insertion of the second clamp member 304 into the body. The set screw 460 may subsequently be driven further into the third channel 334 such that mechanical interaction of the threaded tip 470 with the threading 417 provisionally holds the first and second arms 302, 304 in position over the bone 14. The locking screw 350 is then driven through the second channel 332 and into the first channel 312, threaded engagement between the threaded shaft 356 and the threads of the first channel 312 drawing the first and second clamp members 302, 302 toward one another and applying a radially compressive force to the bone 14. As those skilled in the art will understand, the set screw 460 and the locking screw 350 may each need to be adjusted any number of times to achieve a desired tightening of the first and second arms 302, 304 over the bone 14. In an alternate embodiment, the locking screw 350 may be removed from the assembly 400 such that only the set screw 460 applies a compressive force to the bone 14.

Figure 10:
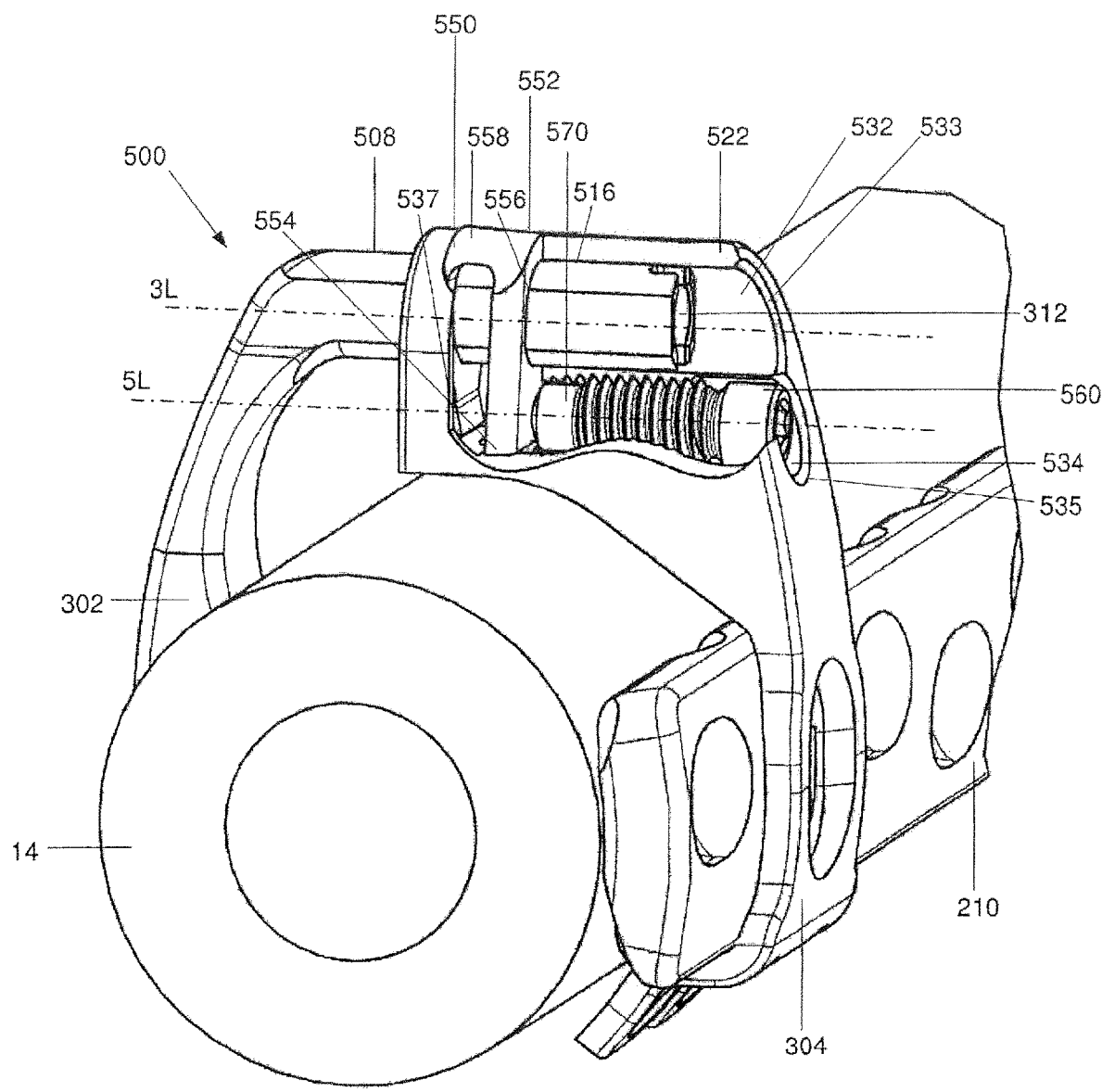
FIG. 10 depicts an isometric cutaway view of a bone fixation clamp according to a fourth alternate embodiment of the invention.

The clamp assembly 500 shown in FIG. 10 is substantially similar to the clamp assembly 300 of FIG. 8, with like elements referenced with like reference numerals. The clamp assembly 500 includes first and second clamp members 302, 304 including first and second arms 508, 522. The second arm 522 includes the second channel 532 and a third channel 534. The second channel 532 is substantially similar to the second channel 332 and extends through the second arm 522 from a first end 533 to a second end (not shown) open to an end of the second arm 522. The third channel 534 extends through the second arm 522 from a first end 535 and along a longitudinal axis 5L substantially parallel to the axis 3L to a second end 537 within the second arm 522. The third channel 534 is dimensioned to receive therethrough a set screw 560 substantially similar to the set screw 360 but having a substantially blunt, non-threaded distal tip 380. The third channel 534 may include threading configured to threadedly engage a threaded shaft of the set screw 560.

The second arm 522 further includes a tab 550 therein intersecting the second and third channels 532, 534. The tab 550 extends from a first end 552 connected to an outer wall of the second arm 522 adjacent the second channel 532 to a free end 554 within the third channel 534. In a region intersecting the second channel 532, the tab 550 includes an opening 556 having an opening axis substantially aligned with the axis 3L to permit insertion of the first arm 508 therethrough. In a region intersecting the third channel 534, the tab 550 is substantially planar and is dimensioned to prevent the set screw 560 from moving therepast, as will be described in greater detail with respect to the exemplary method below. The tab 550 is attached only to the outer wall of the second arm 522 at the first end 552 and is therefore substantially deflectable within a range selected to permit the tab 550 to apply a predetermined pressure on the first arm 508 in an operative configuration, as will also be described in greater detail below. The tab 550 further comprises an extension 558 configured and dimensioned to separate the free end 554 from the second end 537 of the third channel 534 by a predetermined distance, a length of the extension conforming to a permitted range of deflection of the free end 554.

In accordance with an exemplary method of use of the clamp assembly 500, the set screw 560 is partially inserted into the third channel 534 such that the blunt tip 570 is separated from the tab 550. The first and second clamp members 302, 304 are then inserted into the body such that the first arm 508 is slidably inserted into the second channel 532 and the arcuate bodies 310, 326 contact an outer surface of the bone 14. The set screw 560 is then advanced further into the third channel 534 until the blunt tip 570 abuts the tab 550. Further driving of the set screw 560 causes a deflection of the tab 550 toward the second end 537. The deflection causes the opening 556 of the tab 550 to apply a frictional force on the first arm 508 inserted therethrough sufficient to prevent the first arm 508 from moving relative to the second arm 522. Engagement of the deflected tab 550 with the second end 537 prevents the tab 550 from deflecting out of a predetermined range (i.e. to prevent a fracture of the tab 550 or damage to the first arm 508). The locking screw 350 (not shown) is then inserted through the second channel 532 and into the first channel 312 to draw the first and second clamp members 302, 302 together and apply a radially compressive force to the bone 14.

Figure 11:
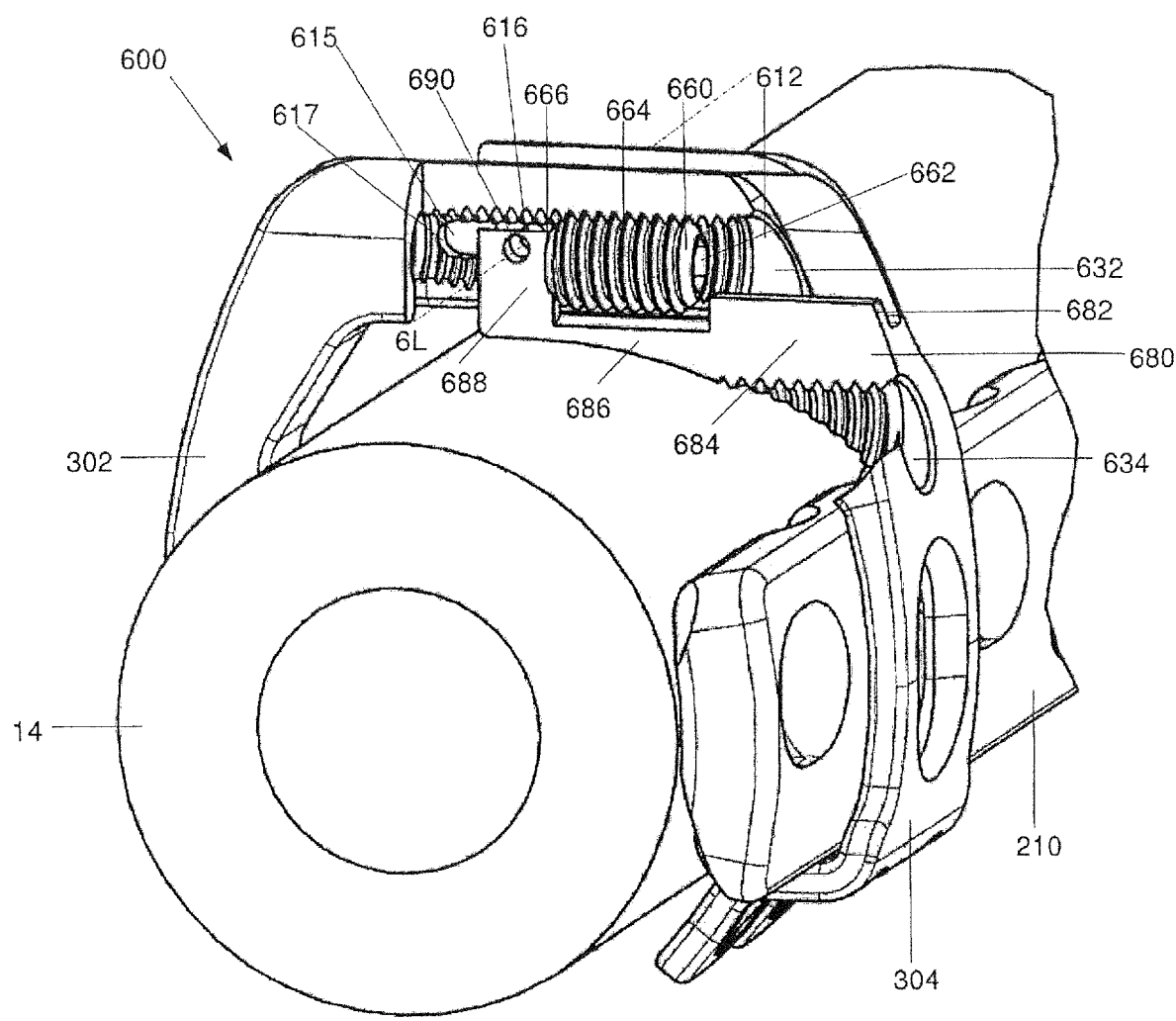
FIG. 11 depicts an isometric cutaway view of a bone fixation clamp according to a fifth alternate embodiment of the invention.

The clamp assembly 600 shown in FIG. 11 is substantially similar to the clamp assembly 300 of FIG. 8, wherein like elements are referenced with like reference numerals. The clamp assembly 600 includes first and second clamp members 302, 304 including first and second arms 608, 622. The first arm 608 is substantially similar to the first arm 608 and includes the channel 312 having threading 614. A cross-bore 615 extends through the first arm 608 along an elongated cross-bore axis extending substantially orthogonal to the longitudinal axis 3L of the first channel 612 from a first end 616 to a second end 617. In an exemplary embodiment, the cross-bore 615 extends through both outer walls of the first arm 608 so that a pin (not shown) inserted therethrough and through a pin bore 690 effectively locks the first and second clamp members 302, 304 to one another, as will be described in greater detail later on. In another embodiment, however, the cross-bore 615 may extend through only one wall of the first arm 608 without deviating from the scope of the invention. In an exemplary embodiment, the cross-bore 615 has a length of approximately 30±4 mm to define a corresponding range of movement of the first and second clamp members 302, 304 toward and away from one another.

The second arm 622 includes a second channel 632 extending therethrough and substantially similar to the second channel 332 of FIG. 8. A screw 660 is housed completely within the second channel 632 in an operative configuration. The screw 660 extends from a first end including a driver-engaging recess 662 and along an elongated threaded shaft 664 to a second end 666. The second channel 632 further includes a longitudinal slot (not shown) permitting a wall 680 to extending therethrough and into the second channel 632 to substantially bisect the second channel 632. The wall 680 extends from a first end 682 and includes a first wall portion 684 having a first height. In an exemplary embodiment, the first height is selected to prevent the screw 660 from moving therepast out of the second channel 632 while also permitting a driving mechanism (not shown) to be inserted therepast to permit driving of the screw 660. A second wall portion 686 of the wall 680 extending away from the first wall portion 684 is formed with a height selected to prevent extension thereof into the second channel 632. A length of the second wall portion 686 is substantially equivalent to a length of the screw 660 to permit the screw 660 to be seated between the first wall portion 684 and a third wall portion 688. The third wall portion 688 extends into the second channel 632 by a distance selected to prevent movement of the screw 660 therepast such that a pin bore 690 extending therethrough along an axis 6L aligns with the cross-bore 615. A diameter of the pin bore 690 is substantially equivalent to a diameter of a pin (not shown) inserted therethrough in an assembled configuration. Specifically, the pin (not shown) extends through the cross-bore 615 and pin bore 690 along the axis 6L and is permanently secured to the clamp assembly 600 (i.e., during manufacturing). The pin (not shown) is axially movable along a length of the cross-bore 615, which defines a desired range of movement of the first and second clamp members 302, 304 relative to one another in a direction substantially perpendicular to a longitudinal axis of the bone 14.

The second clamp member 304 also comprises a third channel 634 extending into the arcuate body portion 326 separate from the relief recess 336. The third channel 634 is threaded and configured to engage a positioning tool (not shown) to provisionally clamp the clamp assembly 600 to the bone 14.

In accordance with an exemplary method of use of the clamp assembly 600, the positioning tool (not shown) is inserted through the third channel 634 to provisionally hold the assembly 600 over the bone 14. In a first insertion configuration, the pin (not shown) and pin bore 690 are positioned toward the first end 616 of the cross-bore 615 so that the first and second clamp members are moved radially away from one another to permit insertion thereof over the bone 14. A driving mechanism (not shown) is then inserted into the recess 662 to drive the screw 660 forward, causing the pin (not shown) to advance toward the second end 617 of the cross-bore 615. As described above, positioning of the screw 660 between the first wall portion 684 and the third wall portion 688 prevents loss of the screw 660 in soft-tissue of the body. This movement causes the first and second clamp members 302, 304 to move radially inward to apply a radially compressive force to the bone 14.

Figure 12:
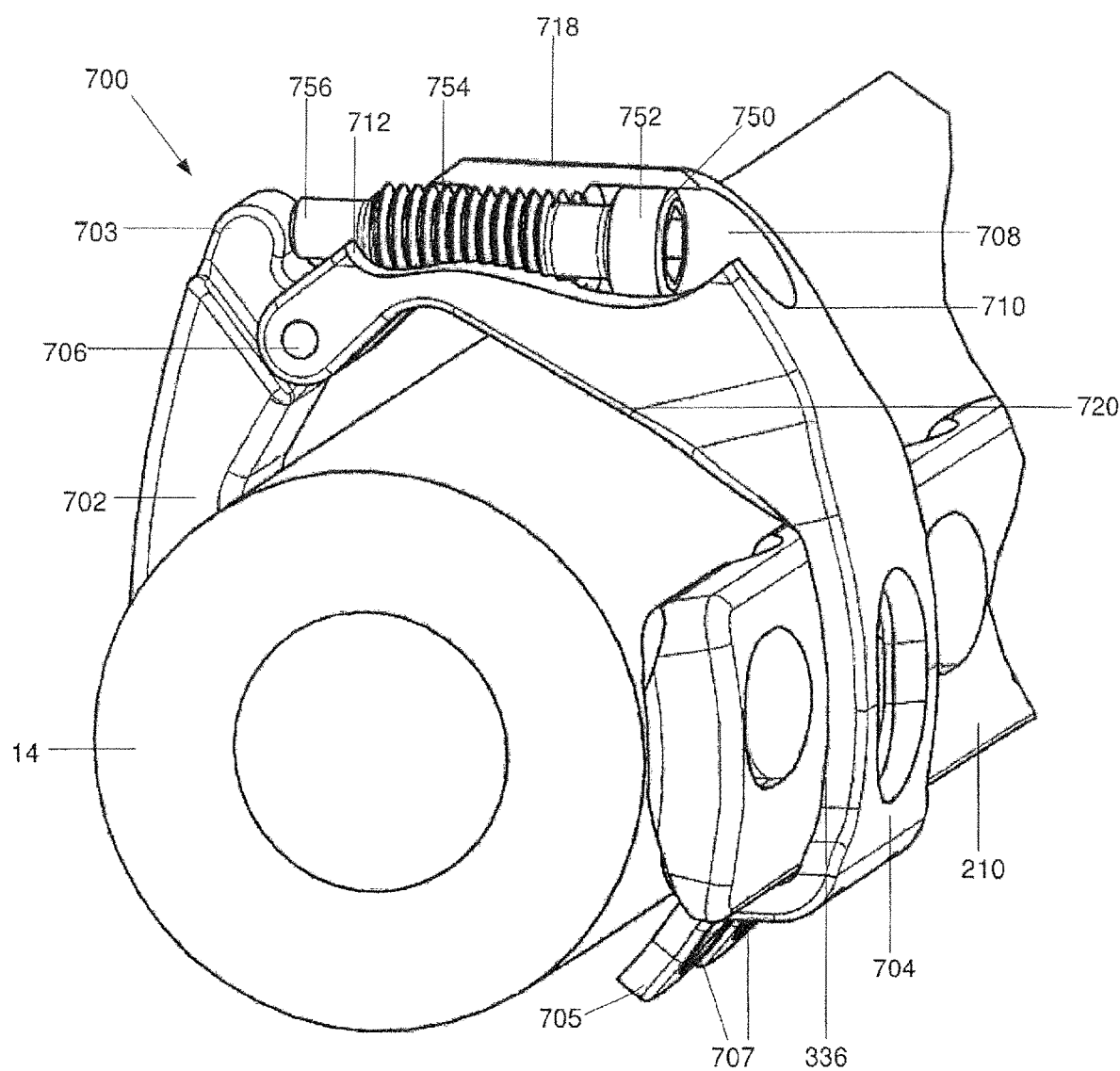
FIG. 12 depicts an isometric cutaway view of a bone fixation clamp according to a sixth alternate embodiment of the invention.

The clamp assembly 700 shown in FIG. 12 is substantially similar to the clamp assembly 300 of FIG. 8, with like elements are referenced with like reference numerals. However, whereas the clamp assemblies 300-600 are slidably brought into engagement with one another, the exemplary embodiment of FIG. 12 includes first and second clamp members 702, 704 pivotally attached to one another about a pivot axis of a pivot pin 706. The first and second clamp members 702, 704 are each substantially arcuate conform generally to a contour of an outer surface of the bone 14. The second clamp member 704 includes a relief recess 336 to house the bone plate 210, as described in greater detail earlier. The pivot pin 706 may be permanently attached to the first and second clamp members 702, 704 (e.g., via a laser weld, etc.) to permit pivotal movement of the first and second clamp members 702, 704 relative to one another within a predetermined angular range.

The second clamp member 704 includes a channel 708 extending therethrough from a first end 710 to a second end 712. A portion of the channel 708 is threaded to threadedly receive a screw 750 therethrough. The screw 750 extends from a first end including a head 752 and along a threaded shaft 754 to a non-threaded, substantially blunted second end 756. In an exemplary embodiment, the channel 708 includes a first channel portion 714 having a first diameter and a second channel portion 716 having a second diameter smaller than the first diameter. The second channel portion 716 is dimensioned to prevent movement of the head 752 thereinto to define a maximum insertion depth of the screw 750 within the channel 708. In a first exemplary embodiment, the channel 708 is positioned adjacent an outer surface 718 of the second clamp member 704 so that the screw 750 is positioned laterally of the pivot pin 706. Insertion of the screw 750 into the channel 708 thereby applies a compressive force to an outer surface of the first clamp member 702 having an abutment 703, as will be described in greater detail with respect to the exemplary method below. In another embodiment (not shown), the channel 708 may be positioned adjacent a surface 720 of the second clamp surface configured to lie adjacent an outer surface of the bone 14 in an operative configuration, at least a portion of the surface 720 coming into direct contact with the bone 14. In this embodiment, the screw 750 inserted through the channel 708 may come into contact with a first portion of bone-contacting surface of the first clamp member 702. The first portion of the bone-contacting surface may be angled and dimensioned such that the force applied thereto by the screw 750 forces the first clamp member 702 to a radially compressive configuration over the bone 14. Those skilled in the art will understand that, alternatively, the screw 750 may extend into a threaded opening in the second clamp member 704 so that interaction between a threaded surface of the opening and the screw 750 pivots the second clamp member 704 relative to the first clamp member 702.

In one embodiment of the invention, the first and second clamp members 702, 704 may have a substantially uniform width and thickness. In another embodiment, portions of the first and second clamp members 702, 704 configured to directly contact the hone 14 in the operative configuration may have an increased thickness to increase a contacting surface area thereof with the bone 14. A free end 705 of the second clamp member 704 further comprises one or more plate holes 707 extending therethrough, the plate holes 707 permitting passage of bone screws (not shown) therethrough and into the bone 14. As those skilled in the art will understand, these hone screws (not shown) provide an additional mechanism to secure the assembly 700 to the bone 14.

In accordance with an exemplary method according to the invention, the first and second clamp members 702, 704 are positioned over a target portion the bone 14. The screw 750 may be pre-loaded onto the clamp assembly 700 prior to insertion thereof into the body (i.e., in a retracted position in which the second end 756 does not extend out of the second end 712 of the channel 708 or is otherwise separated from an abutment 703). In another embodiment, the screw 750 may be inserted into the body after the clamp assembly 700 has been provisionally positioned over the bone 14. In an exemplary embodiment, the assembly 700 may include a biasing member (e.g., a spring-loaded element) biasing the first and second clamp members 702, 704 toward a radially expanded configuration to aid in positioning of the clamp assembly 700 over the bone 14. As those skilled in the art will understand, the first and second clamp members 702, 704 may be pivoted through a predetermined range of angles relative to one another prior to insertion of the screw 750 to permit insertion of the clamp assembly 700 over the bone 14, a maximum opening angle of the first and second clamp members 702, 704 being an angle at which the abutment 703 contacts the second end 712 of the opening 708. The screw 750 may then be advanced into the channel 708 until the distal end 756 contacts an abutment 703 extending from the first clamp member 702. As the screw 750 is advanced, engagement of the distal end 756 with the abutment 703 forces the first clamp member 702 to pivot about the pin 706 closing the first and second clamp members 702, 704, respectively, over the bone 14 and increasing a compressive hold of the clamp assembly 700 on the bone 14.

It will be apparent to those skilled in the art that various modifications and variations can be made in the structure and the methodology of the present invention, without departing from the spirit or the scope of the invention. Thus, it is intended that the present invention cover the modifications and the variations of this invention provided that they come within the scope of the appended claims and their equivalents.

What is claimed is:

1. A bone fixation clamp, comprising:
a first arcuate clamp member configured to conform to a shape of a target portion of a bone and extending between a first end having a first connection portion to a first free end, the first connection portion having a first channel extending therethrough and an extension portion extending from the first connection portion;
a second arcuate clamp member configured to conform to a shape of the target portion of the bone and extending between a second end having a second connection portion and a second free end, the second connection portion having a second channel extending therethrough and an upper and a lower flanged configured to form an opening therebetween to receive the extension portion from the first connection portion into the opening; and
an adjustment member inserted through the first channel and passing into the second channel so that, as the adjustment member is inserted into the second channel, the first arcuate clamp member is drawn toward the second arcuate clamp member to apply a radially compressive force to the bone.

2. The bone fixation clamp of claim 1, wherein the first connection portion is pivotally coupled to the second connection portion.

3. The bone fixation clamp of claim 2, wherein the first connection portion is hinged to the second connection portion by a hinge or pivot pin.

4. The bone fixation clamp of claim 1, further comprising a biasing member coupled between the first and second connection portions to bias the first and second clamp members toward a radially expanded configuration.

5. The bone fixation clamp of claim 4, where the biasing member is a spring.

6. The bone fixation clamp of claim 1, wherein the first and second channels are internally threaded, and the adjustment member is threaded to correspondingly engage the internal threading of the first channel and into the internal threading of the second channel.

7. The bone fixation clamp of claim 1, wherein the first arcuate clamp member comprises a first concave inner surface configured to conform to the shape of the target portion of the bone, and the second arcuate clamp member comprises a second concave inner surface configured to conform to the shape of the target portion of the bone.

8. The bone fixation clamp of claim 7, wherein the first concave inner surface comprises at least one spike-like protrusion extending outwardly from the first concave inner surface configured to engage a surface of the target portion of the bone.

9. The bone fixation clamp of claim 8, wherein the radially compressive force pushes the spike-like protrusion of the first concave inner surface into the surface of the target portion of the bone.

10. The bone fixation clamp of claim 8, wherein the second concave inner surface comprises at least one spike-like protrusion extending outwardly from the second concave inner surface configured to engage the surface of the target portion of the bone.

11. The bone fixation clamp of claim 10, wherein the radially compressive force pushes the spike-like protrusion of the second concave inner surface into the surface of the target portion of the bone.

12. The bone fixation clamp of claim 7, further comprising at least one pressure relief recess formed on at least one of the first concave inner surface and the second concave inner surface, the pressure relief recess is configured to preserve blood flow therethrough when the first and second arcuate clamp members are radially compressed against the bone.

13. The bone fixation clamp of claim 1, wherein the first channel extends through the extension portion of the first arcuate clamp member.

14. The bone fixation clamp of claim 1, further comprising a third channel extending through at least one of the first and second arcuate clamp members.

15. The bone fixation clamp of claim 14, wherein the third channel is internally threaded.

16. The bone fixation clamp of claim 15, further comprising an externally threaded anchoring screw configured to correspondingly engage the internal threading of the third channel and into the bone to anchor the fixation clamp to the target portion of the bone.

17. The bone fixation clamp of claim 1, wherein the bone is a long bone.

18. A system for bone fixation, comprising:
a bone plate comprising an elongated plate member extending from an upper end having a trochanteric grip portion to a free lower end, the trochanteric grip portion comprising an internally threaded aperture;
a bone fixation clamp comprising a first arcuate clamp member configured to conform to a shape of a target portion of a bone and extending between a first end having a first connection portion to a first free end, the first connection portion having a first channel extending therethrough, a second arcuate clamp member configured to conform to a shape of the target portion of the bone and extending between a second end having a second connection portion and a second free end, the second connection portion having a second channel extending therethrough, an adjustment member inserted through the first channel and passing into the second channel so that, as the adjustment member is inserted into the second channel, the first arcuate clamp member is drawn toward the second arcuate clamp member to apply a radially compressive force to the bone, and an internally threaded third channel extending through at least one of the first and second arcuate clamp members; and
an externally threaded anchoring screw configured to correspondingly engage the internal threading of the third channel and the internally threaded aperture of the trochanteric grip portion and into the bone to anchor the bone fixation clamp to the target portion of the bone.

19. The system of claim 18, wherein the elongated plate member comprises a plurality of internally threaded apertures.

20. The system of claim 18, wherein the bone fixation clamp is configured for placement around the bone and over the elongated plate member.

* * * * *